(12) United States Patent
Bilaus et al.

(10) Patent No.: US 10,099,974 B2
(45) Date of Patent: Oct. 16, 2018

(54) XYLENE ISOMERIZATION

(71) Applicant: KING ABDULLAH UNIVERSITY OF SCIENCE AND TECHNOLOGY, Thuwal (SA)

(72) Inventors: Rakan Sulaiman Bilaus, Thuwal (SA); Ingo Pinnau, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/536,596

(22) PCT Filed: Dec. 16, 2015

(86) PCT No.: PCT/IB2015/002468
§ 371 (c)(1),
(2) Date: Jun. 15, 2017

(87) PCT Pub. No.: WO2016/097855
PCT Pub. Date: Jun. 23, 2016

(65) Prior Publication Data
US 2017/0362143 A1 Dec. 21, 2017

Related U.S. Application Data

(60) Provisional application No. 62/093,020, filed on Dec. 17, 2014.

(51) Int. Cl.
*C07C 5/27* (2006.01)
*B01J 19/24* (2006.01)
(Continued)

(52) U.S. Cl.
CPC .............. *C07C 5/2756* (2013.01); *B01J 8/02* (2013.01); *B01J 19/2475* (2013.01); *B01J 31/06* (2013.01);
(Continued)

(58) Field of Classification Search
CPC . C07C 5/2756; C07C 5/2797; C07C 2531/10; B01J 31/10; B01J 35/065
See application file for complete search history.

(56) References Cited

U.S. PATENT DOCUMENTS 4,101,596 A * 7/1978 Mitchell ............... C07C 5/2737
585/401
4,159,282 A * 6/1979 Olson ................... C07C 5/2775
585/481

(Continued)

OTHER PUBLICATIONS

International Search Report and Written Opinion of Application No. PCT/IB2015/002468 dated Apr. 21, 2016, 11 pages.
(Continued)

*Primary Examiner* — Brian A McCaig
*Assistant Examiner* — Jason Y Chong
(74) *Attorney, Agent, or Firm* — Billion & Armitage; Benjamin C. Armitage

(57) ABSTRACT

A process for producing xylenes, in particular para-xylene that is less energy intensive than conventional processes is provided. In an embodiment the process comprises contacting a feed mixture in an isomerization zone with a catalyst at isomerization conditions and producing an isomerized product comprising a higher proportion of p-xylene than in the feed mixture, wherein the catalyst comprises an acidic sulfonated catalytic membrane. Xylene isomerization can also be coupled with a p-xylene extraction process, where the raffinate (p-xylene deprived stream) from the extraction process is fed to an isomerization reactor to produce p-xylene. In an embodiment, the process can comprise: a) providing a feed stream comprising a mixture of xylene isomers including p-xylene; b) extracting p-xylene from the feed stream using a separator to separate the feed stream into a p-xylene rich stream and a p-xylene deprived stream; and c) delivering the p-xylene deprived stream to an isomeriza-
(Continued)

tion unit, the isomerization unit including an acidic sulfonated catalytic membrane, and using the isomerization unit to produce an isomerized product comprising a higher proportion of p-xylene than in the p-xylene deprived stream delivered to the isomerization unit. In any one or more aspects, the isomerization unit can be operated at a temperature in the range of less than 350°, for example about 20° C. to about 200° C.

14 Claims, 5 Drawing Sheets

(51) Int. Cl.
 B01J 31/06 (2006.01)
 B01J 8/02 (2006.01)
 B01J 31/10 (2006.01)
 B01J 35/06 (2006.01)
(52) U.S. Cl.
 CPC .......... B01J 31/10 (2013.01); C07C 5/2797 (2013.01); B01J 35/065 (2013.01); B01J 2219/0004 (2013.01); C07C 2531/10 (2013.01); Y02P 20/52 (2015.11)

(56) References Cited

U.S. PATENT DOCUMENTS

| | | | | |
|---|---|---|---|---|
| 4,188,282 A | * | 2/1980 | Tabak | B01J 29/44 208/134 |
| 4,420,612 A | * | 12/1983 | Aiba | B01D 61/00 521/139 |
| 6,162,644 A | * | 12/2000 | Choi | G01N 21/359 422/111 |
| 2002/0094466 A1 | * | 7/2002 | Kerres | B01D 67/0041 429/493 |
| 2007/0249882 A1 | * | 10/2007 | Ou | C07C 5/2729 585/478 |

OTHER PUBLICATIONS

Rakan Sulaiman Bilaus: "Membrane 1-16 Materials and Technology for Xylene Isomers Separation and Isomerization via Pervaporation", Nov. 27, 2014 (Nov. 27, 2014), pp. 1-105, XP055258197.

"Membrane Materials and Technology for Xylene Isomers Separation and Isomerization via Pervaporation—KAUST Repository", Nov. 7, 2014 (Nov. 27, 2014), XP055264387, Retrieved from the Internet: URL:http:jjrepository.kaust.edu.sajkaust/handle/10754/336250 [retrieved on Apr. 11, 2016] abstract; 3 pages.

Yeong Y Fetal: "Synthesis, characterization and reactive separation activity of acid-functionalized silicalite-1 catalytic membrane in m-xylene isomerization", Journal of Membrane Science, Elsevier BV, NL, vol. 360, No. 1-2, Sep. 15, 2010 (Sep. 15, 2010), pp. 109-122, XP027118376.

Paolo Beltrame et al: "Isomerization of m-Xylene without Side Reactions, over a Perfluorinated Polymer Sulfonic Acid. A Kinetic Study", Industrial & Engineering Chemistry Research, vol. 19, No. 2, Jun. 1, 1980 (Jun. 1, 1980), pp. 205-208, XP055264408.

* cited by examiner

XYLENE ISOMERIZATION

CROSS-REFERENCE TO RELATED APPLICATION

This application is the National Stage of International Application No. PCT/IB2015/002468, filed 16 Dec. 2015, which claims the benefit of and priority to U.S. Provisional Patent Application No. 62/093,020 entitled "XYLENE ISOMERIZATION", filed on 17 Dec. 2014, all of which are expressly incorporated by reference as if fully set forth herein in their entirety.

TECHNICAL FIELD

The present disclosure generally relates to the production of xylenes, in particular para-xylene or p-xylene.

BACKGROUND

There is increasing demand for xylenes, in particular p-xylene, as starting materials for the manufacture of various plastics and synthetic fibres (such as polyester). Efforts are continually being directed to selectively produce p-xylene from low valued m-xylene and/or o-xylene. Unfortunately, the amount of p-xylene theoretically obtainable from these aromatic compounds is limited by thermodynamics. Attempts to overcome thermodynamic limitations in the transformation of xylenes have constituted a challenge.

A xylene isomerization process has been developed to produce xylenes, in particular p-xylene. It is used intensively in the refining and petrochemical industry. It is an essential process in producing various plastics that use xylenes as precursors.

The current technology focuses on fixed bed reactors having a proprietary catalyst. The catalyst may be a catalytic membrane using zeolite or other inorganic compounds that can be used at the high temperatures in the conventional fixed bed reactor. Exemplary catalysts of the current technology are zeolite catalysts, including for example ZSM-5. The technology, however, is energy intensive, operating at high temperatures and pressures, for example 350° C. to 450° C. and 10-20 bar, and occupies a large footprint.

Accordingly, there is a need to address the aforementioned deficiencies and inadequacies.

SUMMARY

The present disclosure is directed to a process for producing xylenes, in particular para-xylene (or p-xylene) that is less energy intensive than conventional processes. In one or more aspects the present disclosure is directed to a xylene isomerization process that can be carried out at temperatures lower than current technology. Xylene isomerization can also be coupled with a p-xylene extraction process, where the raffinate (p-xylene deprived stream) from the extraction process is fed to an isomerization reactor to produce p-xylene. The mixture of xylenes from the isomerization reactor, or isomerate, can then be recycled back to the p-xylene extraction process to extract the additional p-xylene produced by isomerization, constituting a closed loop system.

In one or more aspects the present disclosure provides a pervaporation process for xylene isomerization carried out at much lower temperature than current technology, resulting in significant energy savings. In one or more aspects, the present disclosure entails use of an acidic sulfonated polymeric membrane for carrying out the xylene isomerization reaction. A suitable membrane can be, for example comprised of a superacid membrane such as Nafion-H. The catalytic membrane can be placed in a catalytic membrane reactor (CMR) designed to carry out the pervaporation process. The performance of the process can be similar to the commercial technology in terms of yields. However, it requires much lower operating temperatures, resulting in large energy savings.

In an embodiment, the present disclosure provides a process for removing p-xylene from a feed stream. The process can comprise the steps of: a) providing a feed stream comprising a mixture of xylene isomers including p-xylene; b) extracting p-xylene from the feed stream using a separator to separate the feed stream into a p-xylene rich stream and a p-xylene deprived stream; c) delivering the p-xylene deprived stream to an isomerization unit, the isomerization unit including an acidic sulfonated catalytic membrane, and using the isomerization unit to produce an isomerized product comprising a higher proportion of p-xylene than in the p-xylene deprived stream delivered to the isomerization unit; and d) admixing the isomerized product with the feed stream for delivery to the separator. In any one or more aspects, the isomerization unit can be operated at a temperature in the range of about 20° C. to about 200° C. The acidic sulfonated catalytic membrane can be comprised of sulfonated polymers and/or copolymers. The isomerization unit can be a catalytic membrane reactor. The isomerization unit can be used to carry out a pervaporation process to produce the isomerized product. The pervaporation process can be carried out under partial vacuum.

In an embodiment, a process is provided for isomerizing a feed mixture comprising xylenes. The process can comprise contacting the feed mixture in an isomerization zone with a catalyst at isomerization conditions and producing an isomerized product comprising a higher proportion of p-xylene than in the feed mixture, wherein the catalyst comprises an acidic sulfonated catalytic membrane. In any one or more aspects, the isomerization zone can be operated at a temperature less than 350° C., less than 300° C. or less than 250° C. In an aspect, the isomerization zone can be operated at a temperature in the range of about 20° C. to about 200° C. The acidic sulfonated catalytic membrane can be comprised of sulfonated polymers and/or copolymers. The isomerization zone can be located within a catalytic membrane reactor. A pervaporation process can be carried out within the isomerization zone. The pervaporation process can be carried out under partial vacuum, for example at a pressure less than 1 bar.

Other systems, methods, features, and advantages of the present process for producing xylene, in particular p-xylene, will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
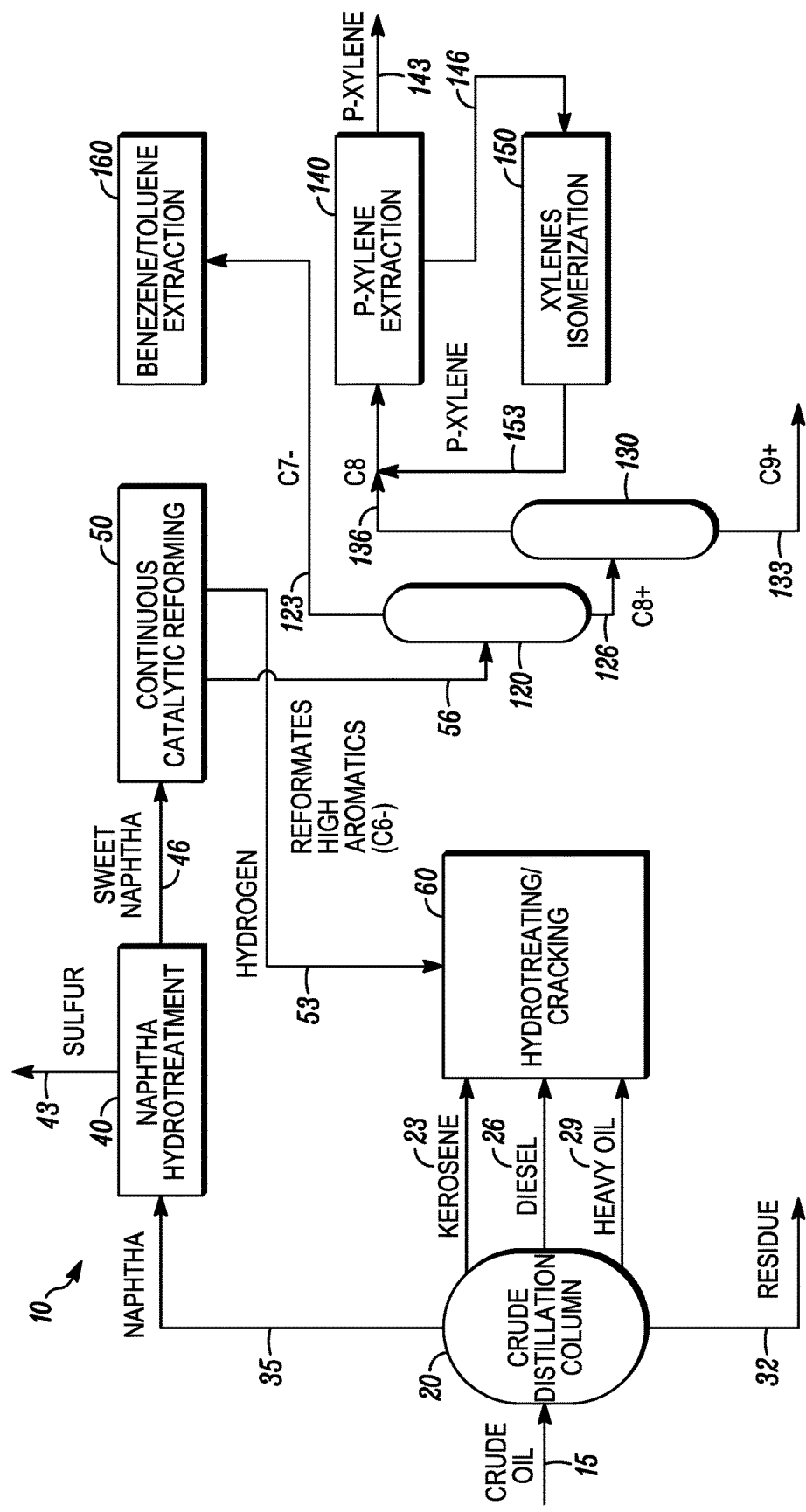
FIG. 1 depicts a process flow diagram for p-xylene production of the present disclosure.

Described below are various embodiments of the present systems and methods for xylene isomerization. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic inorganic chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion

We now provide a discussion of our present disclosure. On the industrial scale, xylene isomerization can be coupled with a p-xylene extraction process, where the raffinate (p-xylene deprived stream) from the p-xylene extractor is fed to an isomerization reactor to produce p-xylene. The mixture of xylenes (isomerate) from the isomerization reactor, including the produced p-xylene, can then recycled back to the p-xylene extraction process to extract the additional p-xylene produced by isomerization, constituting a closed loop system. The initial feed to the system can be, but need not be, catalytically reformed naphthas. The initial feed can include other feeds that contain aromatics that can be fractionated to isolate xylenes. Non-limiting examples of other feeds that can be used include aromatics from steam reforming process units and/or biomass refineries.

An exemplary system 10 is depicted in FIG. 1. Crude oil 15 can be delivered to a distillation column 20 where the crude oil can be separated into any one of a number of various hydrocarbon products from a bottoms product 32, or residue, to an overhead product in the form of naphtha 35. The residue 32 taken from the bottom of the column 20 may be used for example to produce asphalt. Intermediate or mid-products, for example, heavy oils 29, diesel oils 26 and kerosene oils 23, can also be taken from the column 20. The intermediate products can be delivered to reactor 60 for hydrotreating and/or cracking.

The naphtha 35 can consist of a mixture of hydrocarbons generally having between 5 and 12 carbon atoms and having a boiling point between 30° C. and 200° C. Light naphtha can be defined as that fraction boiling between 30° C. and 90° C. and consisting of hydrocarbon molecules having 5 to 6 carbon atoms. Heavy naphtha can be considered or defined as the fraction boiling between 90° C. and 200° C. and consisting of hydrocarbon molecules having 6-12 carbon atoms. The naphtha 35 can be sent to a hydro-treatment reactor 40, where for example sulfur, nitrogen and aromatics can be removed from the naphtha. The hydro-treatment reactor 40 can provide a conventional process wherein the naphtha fractions are reacted with hydrogen in the presence of a catalyst to remove, in particular, sulfur 43 and possibly other components such as nitrogen and aromatics.

The resulting products from the hydro-treatment reactor 40 are sometimes called sweet naphtha. The sweet naphtha 46 having 6 or more carbon atoms (C6+) can then delivered from the hydro-treatment reactor 40 to a catalytic reformer 50 for converting the sweet naphtha 46 into catalytically reformed naphthas. The catalytically reformed naphthas can include high aromatic hydrocarbon molecules having 6 or more carbon atoms (C6+), typically called reformates. The catalytic reformer 50 converts the sweet naphtha and any low—octane linear hydrocarbons (paraffins) into branched alkanes (isoparaffins) and cyclic (aromatic) naphthenes which are then partially dehydrogenated to produce the reformates, for example high aromatic hydrocarbons 56. The catalytic reforming process may also produce light hydrocarbons of lower value, for example hydrocarbon molecules having 5 or less carbon atoms (C5−) such as methane, ethane, propane, butane and pentanes. The reformate high aromatics 56 can include benzene, toluene, and ethylbenzene in addition to the desired xylenes.

The reformates 56 are an example of the aforementioned catalytically reformed naphthas that can be used as an initial feed to separator 120. The process of FIG. 1 up to separator 120 depicts is an example of a conventional process for separating catalytically reformed naphthas. As noted above other feeds that include aromatics that can be fractionated to isolate xylenes can be used for delivery to separator 120.

The aromatics 56 are then delivered to a separator 120 for separating the hydrocarbons having 6 to 7 atoms as an overhead product from those having 8 or more atoms (C8+) as a bottoms product. Included with the lower aromatics having 6 to 7 carbon atoms are benzene and toluene. The low carbon aromatics (C7−) 123 can be delivered to an extractor 160 for extracting benzene and toluene. The bottoms product 126 in the form of higher carbon aromatics having 8 or more carbon atoms (C8+) are delivered to a second separator 130, for example a xylene distillation column, for separating the aromatics having 8 carbon atoms (C8) as an overhead product 136, including in particular xylenes, from a bottoms product 133 in the form of higher order aromatics having 9 or more carbon atoms (C9+). The separator 130 can be another form of a fractional distillation column used to separate xylenes from the higher order aromatics C9+.

Xylene is an aromatic hydrocarbon consisting of benzene ring with two methyl substituents. It has three isomeric forms, 1,2-dimethylbenzene (ortho-xylene, or o-xylene), 1,3-dimethylbenzene (meta-xylene or m-xylene) and 1,4-dimethylbenzene (para-xylene or p-xylene). The overhead product 136, including the xylenes, is delivered to an extractor 140. The extractor 140 extracts para-xylene or p-xylene from the other xylene isomers, namely m-xylene and o-xylene, thus forming a p-xylene rich stream 143 and a p-xylene deprived stream 146 or raffinate. A suitable extractor 140 can include conventional crystallization, selective absorption using chromatographic techniques, such as a simulated moving bed process. The desired p-xylene rich stream 143 can be sent for collection.

The p-xylene deprived stream or raffinate 146 including m-xylene and o-xylene can then be sent to a reactor 150 for carrying out a xylene isomerization process to form p-xylene from the other xylenes, thus forming an isomerized product 153 having a higher proportion of p-xylene than in the p-xylene deprived stream 146 delivered to the isomerization unit or reactor 150. The isomerate 153, including p-xylene, formed in reactor 150 can be admixed with the overhead product 136 from the second separator 130 for recycle to extractor 140 and extraction of p-xylene from the isomerate.

The xylene isomerization process is conventionally carried out using a fixed bed reactor with a proprietary inorganic catalyst, such as the aforementioned heterogeneous catalyst at an operating temperature between 350-450° C. It need not be, however. As noted above this conventional process is energy intensive, operating at high temperatures and pressures and having a large footprint. In contrast, in the present process and system the reactor 150 can include an isomerization unit or an isomerization zone operating at a lower temperature. In one or more aspects, the reactor, and in particular its isomerization zone, can be operated at a temperature less than 350° C., 325° C., 300° C., 275° C., 250° C., 225° C., 200° C., or 190° C. In various aspects the reactor or the isomerization zone can be operated at a temperature in the range of about 20° C. to about 200° C., 25° C. to 200° C., 30° C. to 200° C., 40° C. to 200° C., 50° C. to 200° C., 20° C. to 190° C., 25° C. to 190° C., 30° C. to 190° C., 40° C. to 190° C., or 50° C. to 190° C. In an aspect, the reactor or the isomerization zone can be operated in the range of 70° C. to 80° C., for example at 75° C. as in the example below. An exemplary reactor 150 is a catalytic membrane reactor (CMR).

Accordingly, we have developed a xylene isomerization process for use in the above-described system that is less energy intensive. The xylene isomerization process can be a pervaporation process. As a non-limiting example, the pervaporation process can be a process in which a liquid mixture contacts one side of the membrane (feed), and the permeate is removed as vapor form the other side of the membrane. The driving force for the process is the low vapor pressure on the permeate side of the membrane generated by cooling and condensing the permeate vapor. A partial vacuum can be maintained on the permeate side of the membrane, so that the permeating components are removed as a vapor mixture. In one or more aspects, the pressure on the permeate side can be less than 1 bar. The isomerization reaction occurs in the pervaporation process as the liquid makes contact with the catalytic membrane and the reaction occurs as the product is withdrawn through the membrane as a vapor mixture. The feed is a mixture of xylenes (the p-xylene deprived stream or raffinate 146) and isomerizes at low temperatures and pressures via the catalytic membrane. The permeate becomes a vapor mixture thus forming the isomerate 153 with the higher p-xylene content.

A suitable membrane for use in the isomerization zone of reactor 150 can be an ionomer, such as an acidic sulfonated polymeric membrane. Exemplary membranes are sulfonated polymers and copolymers that we have discovered can be used as an acidic membrane for xylene isomerization. An exemplary ionomer is Nafion, in particular Nafion-H. Nafion-H is a copolymer of a tetrafluoroethylene and perfluorinated sulfonated vinyl ether, which was developed by Du Pont in 1966. Perfluorinated materials have C—F bonds which give them their chemical and thermal stability. Furthermore, the sulfonic acid group combined with a perfluorinated backbone makes Nafion-H very acidic. Nafion-H is known to be a superacid membrane. We have found it to be suitable for catalyzing xylene isomerization for use in reactor 150, in particular for use in a pervaporation process. In addition, thermal and chemical stability of the polymer gives it the ability to maintain the membrane's integrity. Its chemical structure is provided below, and its properties are listed in Table 1.

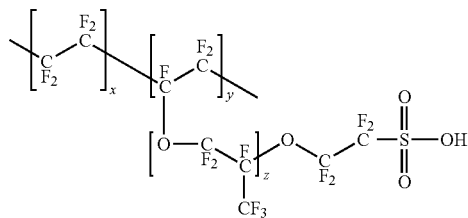

TABLE 1

Properties of Nafion-H.

| | |
|---|---|
| Density (g/cm$^3$) | 1.9 |
| $T_g$ (° C.) | 150 |
| FFV (%) | NA |
| Possible Solvents | Mixture of aliphatic alcohol + water |

Experimental Results

A Nafion-H membrane was tested in a pervaporation set-up, such as described above, as a catalytic membrane reactor process. The membrane was tested for the separation of a 50:50 wt % m/o-xylene mixture at 75° C. The experiment was carried out continuously for more than 80 hours with a total of 4 measurements taken.

Figure 2:
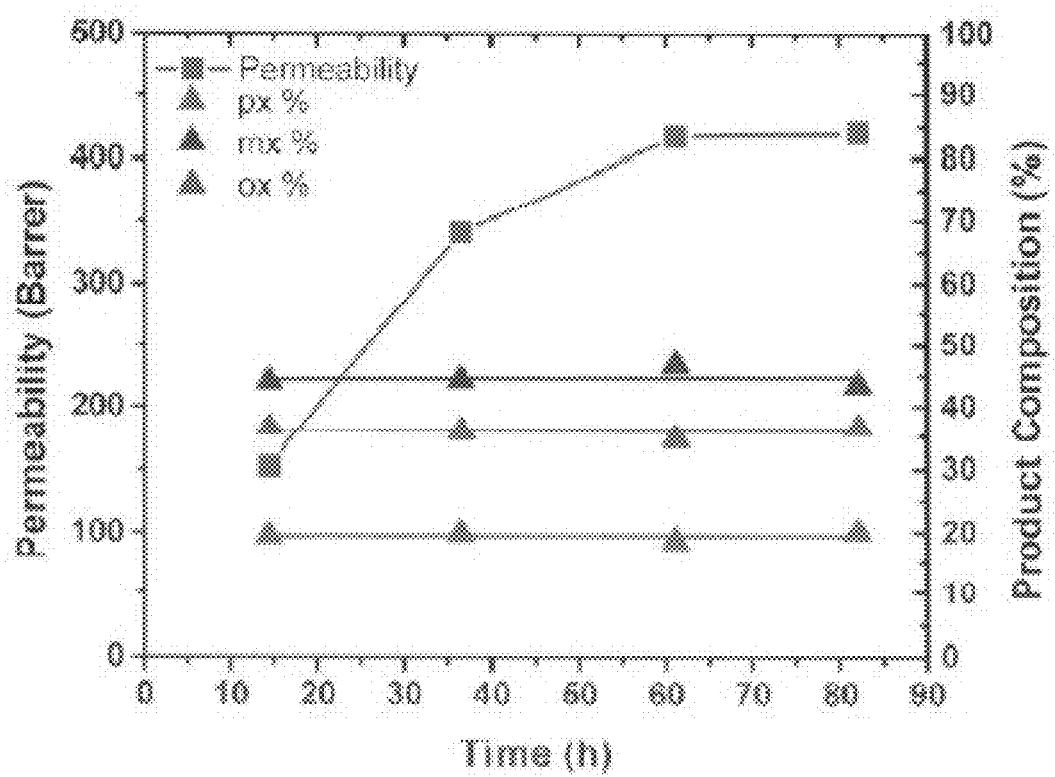
FIG. 2 depicts transport and catalytic properties of Nafion-H for 50:50 m/o-xylene isomerization at 75° C. via pervaporation.

The permeability steadily increased from 152 to 420 Barrer, reaching equilibrium due to swelling of the polymer. Despite this swelling behavior, however, the catalytic activity of the membrane maintained functional, leading to an increase in permeability and a consistent permeate composition. The permeate was analyzed using a gas chromatograph (GC) to determine the percentage of each xylene isomer. The average composition of the permeate was 19.5% p-xylene (px), 44.5% m-xylene (mx), and 36.0% o-xylene (ox). The time dependence of permeability and permeate composition is illustrated in FIG. 2.

Knowing that the isomerization reaction is limited by thermodynamic equilibrium, the product composition achieved downstream the Nafion-H membrane was compared with the thermodynamic equilibrium product distribution in the liquid phase. The achieved composition reaches almost the thermodynamic equilibrium for p-xylene at 75° C., while that of m-xylene is less than the equilibrium value. On the other hand, o-xylene yield is higher than the equilibrium value, as shown in Table 2.

TABLE 2

Nafion-H permeate composition from a 50:50 m/o-xylene mixture at 75° C. compared with thermodynamic equilibrium composition.

| Xylene Isomer | Thermodynamic Equilibrium (%) | Nafion-H (%) |
|---|---|---|
| p-xylene | 20.4 | 19.5 |
| m-xylene | 58.6 | 44.6 |
| o-xylene | 21.0 | 35.9 |

Furthermore, Nafion-H was tested with three different feeds of pure xylenes in order to compare its catalytic performance with a conventional fixed bed reactor and mordenite framework inverted (MFI) zeolite extractor-CMR. The data for the fixed bed reactors and MFI zeolite in CMR used for our comparison is that reported in S. Haag, M. Hanebuth, G. T. P. Mabande, A. Avhale, W. Xchwieger, R. Dittmeyer, *On the use of a catalytic H-ZSM-5 membrane for xylene isomerization*, Micropor Mesopor Mat, 96 (2006) 168-176. Each experiment was carried out under the same conditions using the same pervaporation set-up and a feed temperature of 75° C. However, swelling behavior is apparent in Nafion-H, as the permeability increases gradually over time. The swelling induced by m-xylene and o-xylene is minimal, while the swelling caused by p-xylene is relatively more significant and similar to the swelling induced by the xylenes mixture.

Figure 3:
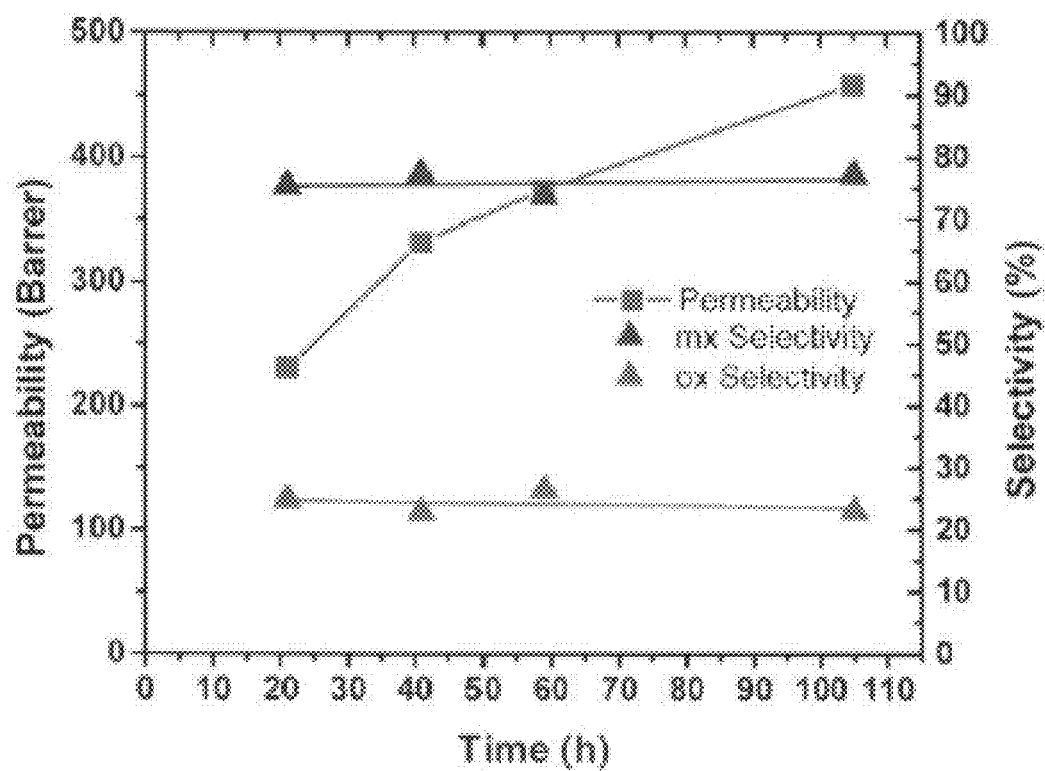
FIG. 3 depicts transport and catalytic properties of Nafion-H for pure p-xylene isomerization at 75° C. via pervaporation.

Pure p-xylene was catalyzed and permeated through Nafion-H at 75° C. via the pervaporation process for more than 100 hours and a total of 4 measurements were taken. The permeability increased from 230 to 458 Barrer due to swelling of the membrane, while the conversion was maintained at an average 26.3%. Selectivity of m-xylene and o-xylene were found to be 75.8% and 24.2%, respectively (FIG. 3).

Figure 4:
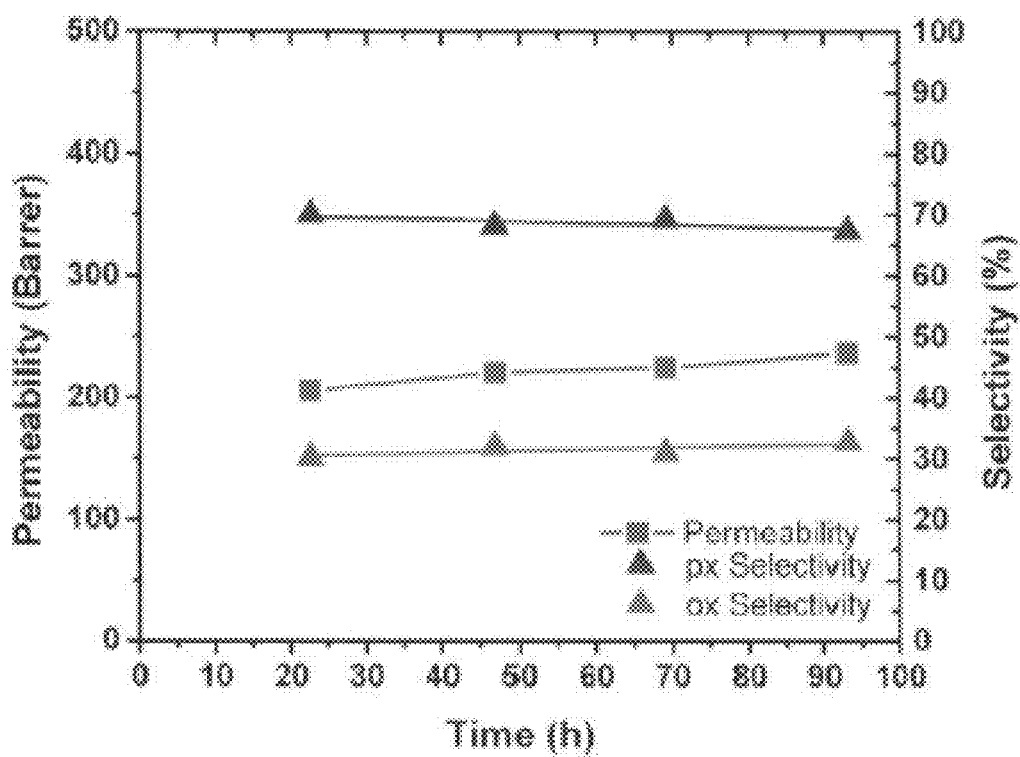
FIG. 4 depicts transport and catalytic properties of Nafion-H for pure m-xylene isomerization at 75° C. via pervaporation.

Pure m-xylene was catalyzed and permeated through Nafion-H at 75° C. via the pervaporation set-up for more than 90 hours and a total of 4 measurements taken. The permeability increased from 206 to 237 Barrer due to swelling of the membrane, while the conversion is maintained at 19.2%. Selectivity of p-xylene and o-xylene were found to be 68.6% and 31.4%, respectively (FIG. 4).

Figure 5:
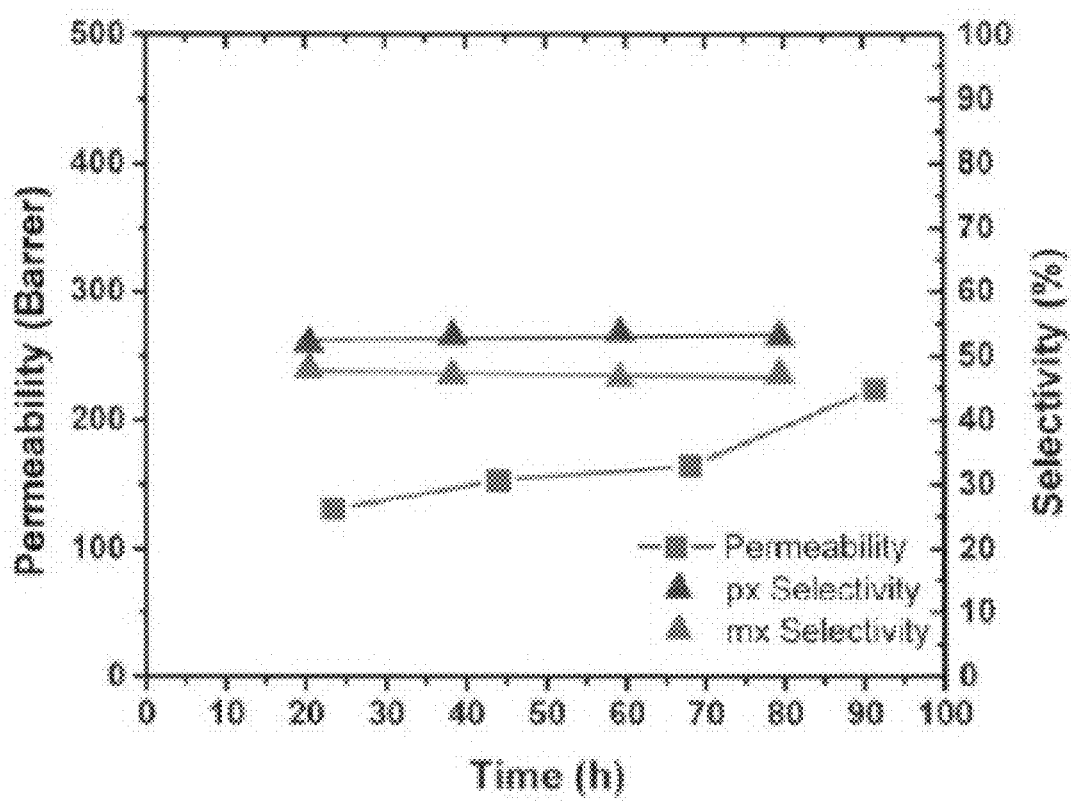
FIG. 5 depicts transport and catalytic properties of Nafion-H for pure o-xylene isomerization at 75° C. via pervaporation.

Pure o-xylene was catalyzed and permeated through Nafion-H at 75° C. via the pervaporation process for more than 90 hours and a total of 4 measurements were taken. The permeability increased from 130 to 224 Barrer due to swelling of the membrane, while the conversion is maintained at 33.7%. Selectivity of p-xylene and m-xylene were found to be 52.9% and 47.1%, respectively (FIG. 5).

The Nafion-H membrane showed high catalytic activity for xylene isomerization. The results show p-xylene yields very close to the thermodynamic limit when a typical industrial feed of 50:50 m/o-xylene is used as a feed. The superiority of Nafion-H as a catalyst via pervaporation is clearly shown in Table 3.

TABLE 3

Comparison between Nafion-H via pervaporation and H-ZSM-5 membrane via extractor-CMR and fixed bed reactor.

| Membrane Material | Xylene Isomer | p-xylene yield (%) Membrane | FBR | p-xylene selectivity (%) Membrane | FBR |
|---|---|---|---|---|---|
| Catalytic H-ZSM-5 (T = 400° C.) | m-xylene | 6.9 | 5.87 | 66.7 | 55.6 |
| | o-xylene | 7.3 | 6.98 | 30.1 | 30.1 |
| Nafion-H (T = 75° C.) | m-xylene | 13.2 | N/A | 68.6 | N/A |
| | o-xylene | 17.8 | N/A | 52.9 | N/A |

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be also emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

We claim:

1. A process for removing p-xylene from a feed stream, comprising the steps of:
   a) providing a feed stream including a mixture of xylene isomers, wherein the mixture includes at least p-xylene;
   b) extracting p-xylene from the feed stream using an extractor to produce a p-xylene rich stream and a p-xylene deprived stream;
   c) delivering the p-xylene deprived stream to an isomerization unit including an acidic sulfonated catalytic membrane, wherein the membrane includes Nafion-H and is used in an pervaporation process to produce an isomerized product including a higher proportion of p-xylene than in the p-xylene deprived stream delivered to the isomerization unit; and
   d) admixing the isomerized product with the feed stream for delivery to the extractor.

2. The process of claim 1, wherein the isomerization unit is operated at a temperature in the range of about 20° C. to about 200° C.

3. The process of claim 1, wherein the feed stream further includes aromatics used to isolate xylenes.

4. The process of claim 3, wherein the feed stream includes one or more of catalytically reformed naphthas, aromatics from a stream reforming process, and aromatics from biomass refineries.

5. The process of claim 1, wherein the isomerization unit is a catalytic membrane reactor.

6. The process of claim 1, wherein the isomerization unit is operated at a temperature in the range of about 70° C. to about 80° C.

7. A process for isomerizing a feed mixture including xylenes, the process comprising:
   contacting the feed mixture with an acidic sulfonated catalytic membrane including Nafion-H at isomerization conditions in an isomerization zone, wherein a pervaporation process using the membrane is carried out within the isomerization zone; and
   producing an isomerized product including a higher proportion of p-xylene than in the feed mixture.

8. The process of claim 7, wherein the isomerization zone is operated at a temperature in the range of about 20° C. to about 200° C.

9. The process of claim 7, wherein the feed stream includes aromatics used to isolate xylenes.

10. The process of claim 9, wherein the feed stream includes one or more of catalytically reformed naphthas, aromatics from a stream reforming process, and aromatics from biomass refineries.

11. The process of claim 7, wherein the isomerization zone is located within a catalytic membrane reactor.

12. A process for isomerizing a feed mixture including xylenes, comprising:
   contacting the feed mixture with a catalyst at isomerization conditions in an isomerization zone to produce an isomerized product including a higher proportion of p-xylene than in the feed mixture, wherein the catalyst includes a superacidic sulfonated ionomeric membrane including Nafion-H, wherein the isomerization unit is operated at a temperature in the range of about 70° C. to about 80° C.

13. The process of claim 12, wherein the feed mixture further includes aromatics used to isolate xylenes.

14. The process of claim 12, wherein the feed mixture further includes one or more of catalytically reformed naphthas, aromatics from a steam reforming process, and aromatics from biomass refineries.

* * * * *